United States Patent [19]

Bloch

[11] 4,183,103
[45] Jan. 15, 1980

[54] PROSTHETIC ONE-WAY HEART VALVE

[76] Inventor: Eric Bloch, 556 W. 141st St., New York, N.Y. 10031

[21] Appl. No.: 920,302

[22] Filed: Jun. 29, 1978

[51] Int. Cl.² ............................................. A61F 1/22
[52] U.S. Cl. ...................................... 3/1.5; 137/527.8
[58] Field of Search ........................................ 3/1.5, 1; 137/527–527.8

[56] References Cited

U.S. PATENT DOCUMENTS

| | | | |
|---|---|---|---|
| 3,476,143 | 11/1969 | Kaster | 3/1.5 X |
| 3,824,629 | 7/1974 | Shiley | 3/1.5 |
| 3,835,475 | 9/1974 | Child | 3/1.5 |
| 3,953,898 | 5/1976 | Bloch | 3/1.5 |
| 4,057,857 | 11/1977 | Fettel | 3/1.5 |

Primary Examiner—Ronald L. Frinks
Attorney, Agent, or Firm—Alan H. Levine

[57] ABSTRACT

A heart valve including a generally annular body and a disc within the body. A ring-like protuberance projects from one face of the disc, and a fulcrum member projecting into the central opening of the valve body engages the inner surface of the protuberance. The disc pivots about the fulcrum member, to open and close the valve, and fits loosely between the fulcrum member and retaining elements so that the disc can rotate in its own plane. The rig-like protuberance defines an abutment responsive to fluid flowing in the no-flow direction of the valve for aiding pivotal movement of the disc to close the valve. An upstanding continuous wall on the face of the disc opposite the protuberance responds to fluid flow in the flow direction of the valve for aiding the pivotal movement of the disc to open the valve. The fulcrum member carries a guide plate which cooperates with the free end of the fulcrum means for preventing movement of the disc in its own plane when the valve is closed.

12 Claims, 16 Drawing Figures

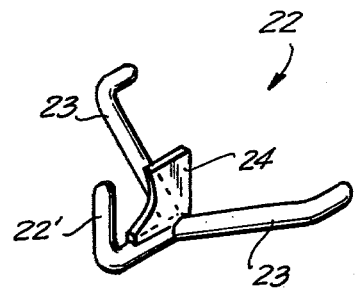
FIG. 4
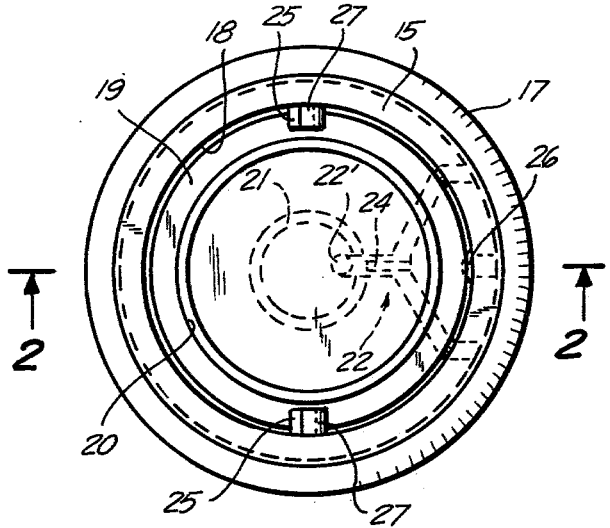
FIG. 1
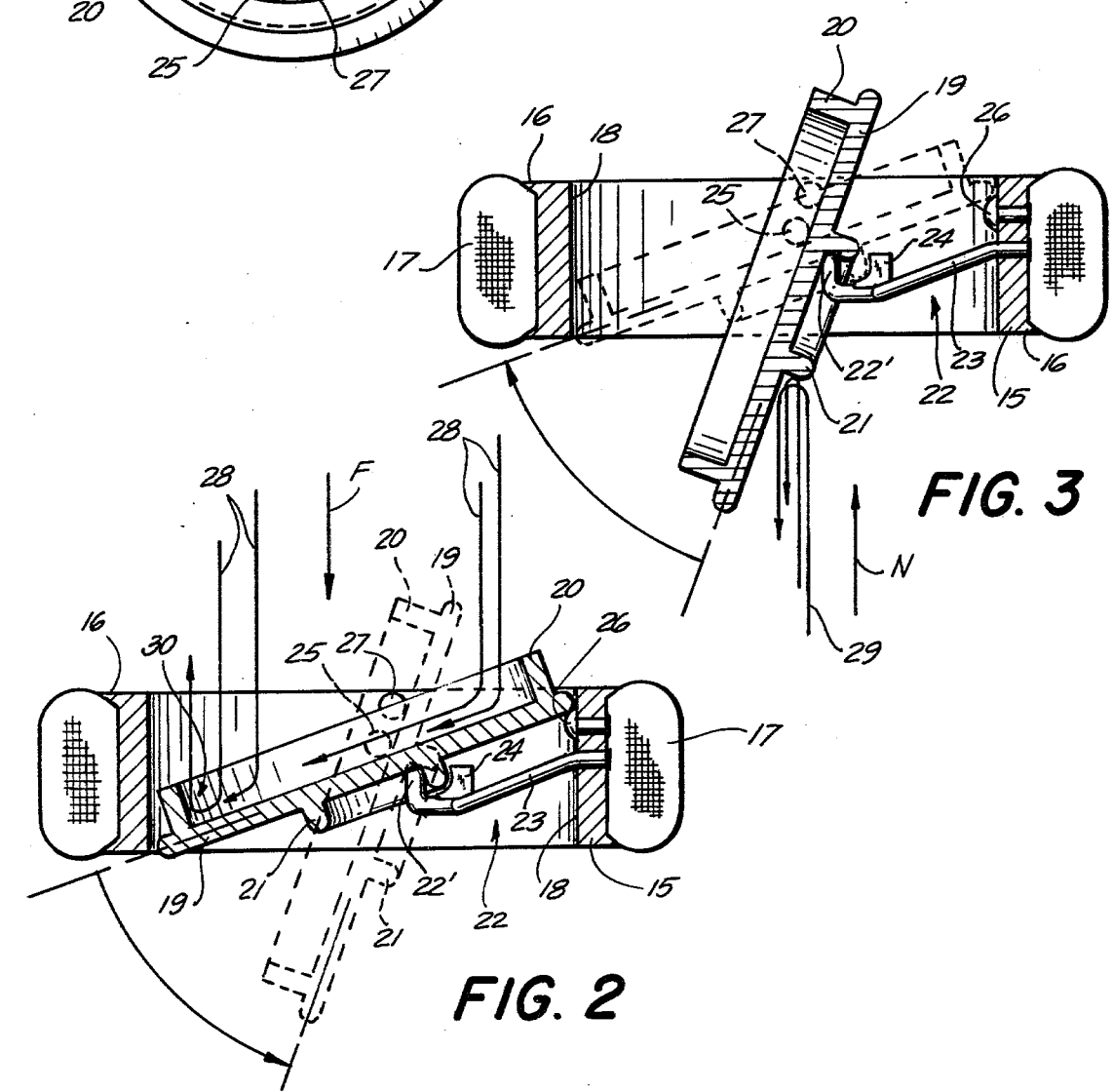
FIG. 3
FIG. 2

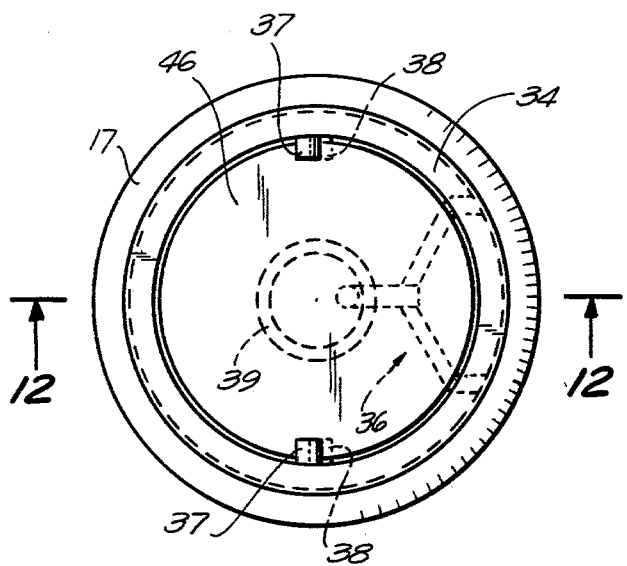
FIG. 11
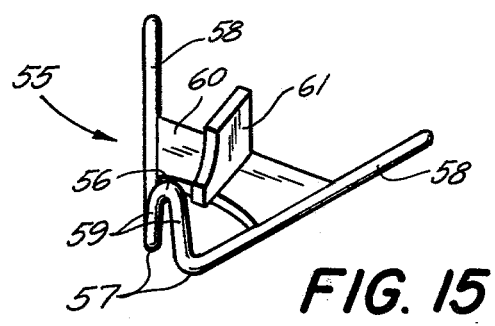
FIG. 15
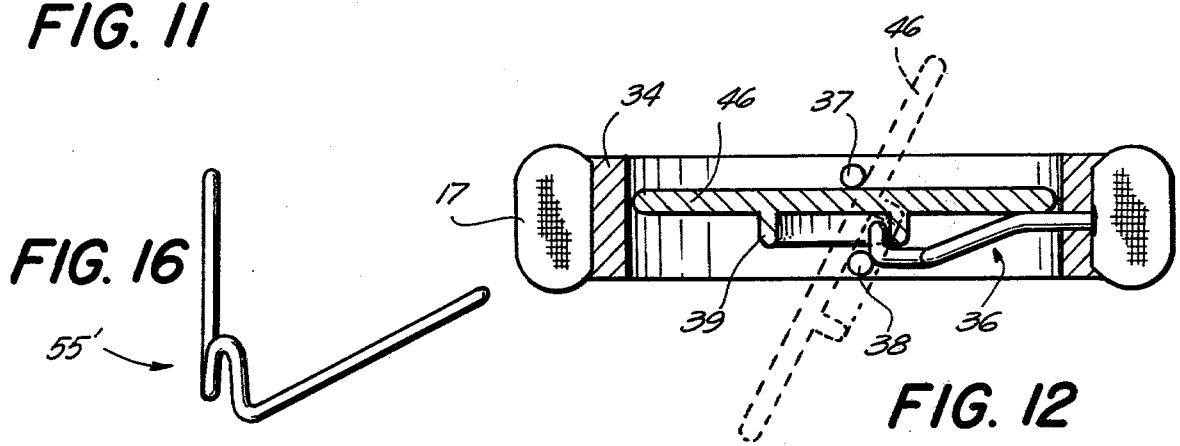
FIG. 16
FIG. 12
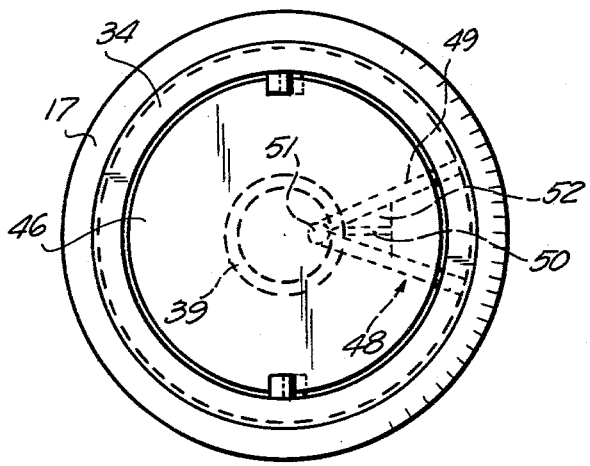
FIG. 13
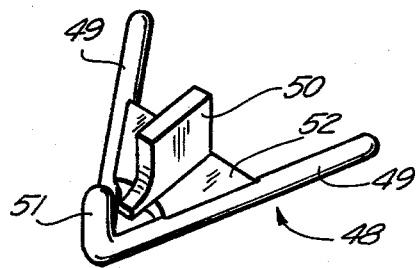
FIG. 14

PROSTHETIC ONE-WAY HEART VALVE

The present invention relates to an artificial valve that is intended to be inserted into the human heart to replace a defective natural valve, and represents in certain respects an improvement over the valve shown and described in U.S. Pat. No. 3,953,898.

Certain embodiments of the valve illustrated in U.S. Pat. No. 3,953,898, particularly those of FIGS. 5-8 and 11 and 12, allow the disc arranged within the annular valve body, not only to pivot between open and closed positions, but also to rotate in its own plane, which helps the valve to be continuously self-cleaned as blood flows through it.

Furthermore, a series of upstanding fins or ridges, preferably spaced apart, are arranged on the surface of the disc. The purpose of these upstanding vanes is to define a pocket-like arrangement for catching blood flowing against vanes to produce a turbine effect which quickly swings the disc to its open position. The vanes are spaced apart to leave openings through which blood, flowing into the pocket, can leave. The pocket is therefore self-cleaning and formation of blood clots within the pocket is prevented. The valve also includes a baffle plate on its downstream end, which is used to speed up the pivoting motion of the disc from open to closed position.

While the valve of U.S. Pat. No. 3,953,898 functions completely satisfactorily, a simpler design would be easier to manufacture. For example, the embodiment of the valve consisting of a pivoting disc having a series of upstanding fins, spaced apart and arranged in a circle, is somewhat complicated and expensive to manufacture. Furthermore use of the baffle plate on the downstream end of the valve enlarges the overall width of the design, adds considerably to the cost of producing the valve, and substantially increases the weight of the product.

The objects of the present invention are, therefore, to provide an improved valve which is less complicated and expensive to manufacture, to provide a valve which consists of fewer individual parts, to provide a valve which is of considerably narrower width and considerably less weight, and to provide a valve which in addition to these merits still preserves the best features and advantages of the valve shown in U.S. Pat. No. 3,953,898.

The valve of this invention comprises an annular valve body having an opening therein allowing blood to flow through the valve. A disc-type valve member is located inside the valve body and is pivotally supported within the valve body by holding means which permit the disc to swing around an imaginary axis for opening and closing the valve. On the downstream side of the disc is a circular protuberance. The inner surface of the protuberance is engaged by a hook-like fulcrum member projecting from the valve body, the fulcrum member supporting the disc and at the same time allowing the disc to swing freely between open and closed positions. The disc is also permitted to rotate in its own plane during the operation of the valve. The hook-like fulcrum member carries a guide device, in the form of a plate, which cooperates with the protuberance to prevent the disc, when in its closed position, from vibrating or wobbling under the pressure of the blood.

In one embodiment of the invention, there is fixed to the face of the disc a ring or tube-like flat rim projecting generally upstrem, i.e., in a direction opposite to the flow direction through the valve. The purpose of this rim is to collect inflowing blood and cause the disc to swing open very fast. The pivoting disc may be positioned at an acute angle to the plane of the valve body when in closed condition. Alternatively, the pivoting disc may be in a horizontal position, when the valve is closed. This makes it possible to construct a very light weight valve, also having at the same time a very low profile.

The invention will be better understood and additional objects and advantages will become apparent from the following description of the preferred embodiments illustrated in the accompanying drawings. Various changes may be made in the details of construction and arrangement of parts and certain features may be used without others. All such modifications within the scope of the appended claims are included in the invention.

In the drawings:

FIG. 1 is a plan view of a prosthetic one-way heart valve according to the present invention, the valve being shown in closed condition;

FIG. 2 is a vertical cross-sectional view taken along line 2—2 of FIG. 1;

FIG. 3 is a view similar to FIG. 2, the valve being shown in open condition in solid lines;

FIG. 4 is a perspective view of the fulcrum member of the valve;

FIG. 11 is a plan view of another alternative embodiment of this invention, the valve being shown in closed condition;

FIG. 12 is a cross-sectional view taken along line 12—12 of FIG. 11;

FIG. 13 is a plan view of another embodiment of the invention showing an alternative form of the fulcrum member;

FIG. 14 is a perspective view of the fulcrum member shown in FIG. 13;

FIG. 15 is a perspective view of another alternative form of the fulcrum member; and FIG. 16 is a perspective view of a fulcrum member similar to that of FIG. 15, but without a platform and guide plate.

Figure 5:
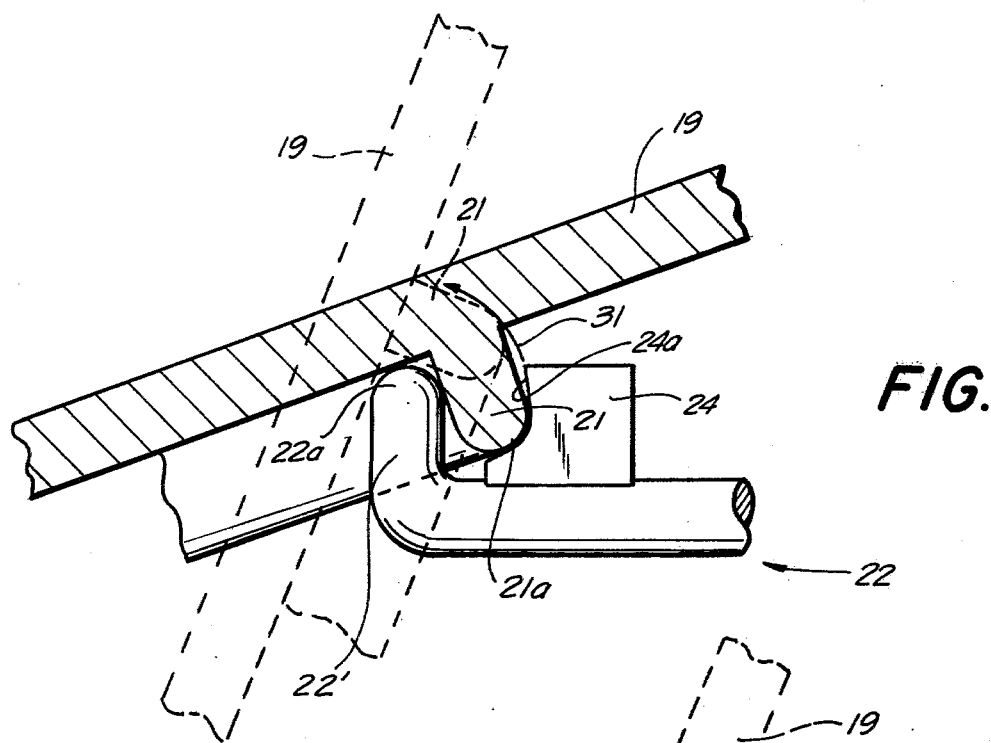
FIG. 5 is a fragmentary view, on an enlarged scale, of a portion of FIG. 2 showing the pivot relationship between the fulcrum member and a ring-like protuberance on the downstream side of the valve disc.

One embodiment of a prosthetic one-way heart valve chosen to illustrate the present invention, and shown in FIGS. 1-4, includes an annular valve body 15 having outwardly projecting peripheal ridges 16 at each end. Surrounding body 15, between ridges 16, is a suture ring 17, by means of which the valve may be sewn into a heart. Body 15 has a central opening 18 defining a blood flow passageway, and a disc 19 is pivotally arranged in this opening to swing between open and closed positions to control flow of blood through the valve.

Disc 19 is of flat design and carries on its upstream face a continuous circular wall or rim 20 projecting generally in a direction opposite to the blood flow through the valve, and arranged close to the periphery of disc 19. Rim 20 defines a kind of pocket for catching blood flowing against disc 19, as will be described in more detail below. Fixed to the downstream face of disc 19 is a circular protuberance 21 concentric with disc 19 and spaced radially inward from the peripheral edge of the disc.

Protuberance 21 cooperates with a fulcrum member 22, projecting into central opening 18 from valve body 15, to define a pivot support for disc 19. Fulcrum member 22 includes two struts 23, fixed to body 15, which merge into a hook-like portion terminating at its free end in a post 22'. The post extends generally in the axial direction of valve body 15, and the free end of the post engages the inner surface of protuberance 21. The horizontal part of the hook-like portion carries an upstanding guide plate 24, the purpose of which will be described below.

Valve body 15 is provided with a pair of retaining pins 25 projecting into the central opening 18 from the inner surface of the valve body 15. Disc 19 fits loosely between the pins 25 and fulcrum member 22 and therefore is able to pivot between its open and closed positions and to rotate in its own plane. Extending into the central opening 18 of the valve body 15 from its inner surface is an abutment 26 defining the position of disc 19 in the closed condition of the valve, as shown in FIG. 2. A pair of abutments 27, projecting inwardly from the inner surface of body 15, define the position of disc 19 in the open condition of the valve, as shown in FIG. 3. Abutment 26 is so placed that when the valve is closed (FIG. 2), disc 19 is arranged at a relatively small acute angle to the plane of the valve body 15. Abutments 27 are so positioned that when the valve is open (FIG. 3), disc 19 is arranged at a relatively large acute angle to the plane of valve body 15. Thus, the positioning of abutments 26 and 27 is such that disc 19 pivots during its entire movement through an acute angle.

In operation, when the valve is in closed condition shown in solid lines in FIG. 2, blood indicated by the arrows 28 flowing toward the valve in the flow direction (arrow F) of the valve, strikes disc 19. Due to the angled condition of the disc, the blood flows along the disc surface into a pocket 30 created by wall 20, which protrudes a turbine effect and swings disc 19 to its open position, shown in broken lines in FIG. 2.

Because the wall 20 is a continuous unbroken tube-like ring, it can be of relatively low height and still perform effectively in catching blood, but also allowing the blood to stream over it, making the wall 20 self-cleaning and avoiding the formation of blood clots. Also, it can be seen that the periphery of disc 19 is spaced slightly from the inner surface of valve body 15 when the valve is closed, so as to prevent disc 19 from becoming wedged in a closed position.

Upon reverse flow of the blood, indicated by arrows 29 in FIG. 3, in the no-flow direction (arrow N) of the valve, the blood flows against a pocket formed by the outer surface of protuberance 21 and disc 19. As a result, disc 19 is swung from the solid line position of FIG. 3 to the broken line position, thereby closing the valve and preventing flow through the valve in the direction indicated by arrow N. Thus, protuberance 21 serves two functions, namely, cooperating with fulcrum post 22' to provide a pivot support for disc 19, and defining, together with the downstream face of disc 19, a pocket against which blood flows thereby creating a turbine effect to swing disc 19 to its closed position.

The pivoting of disc 19 by cooperation of ring-like protuberance 21 with post 22' and the interaction of protuberance 21 with guide 24 is best shown in FIG. 5. During the pivoting of disc 19 the inner surface of protuberance 21 moves around the rounded top 22a of post 22'. Protuberance 21 preferably has a rounded lower edge 21a which is in smooth sliding contact with the curved inner face 24a of guide plate 24 as protuberance 21 moves along the circular path indicated by arrow 31. When the valve is in closed position, shown in solid lines in FIG. 5, the disc is firmly held motionless between guide plate 24 and post 22'. As pointed out before, the pivotable disc 19 is assembled with the valve body in a floating way allowing the disc to rotate in its own plane. The rotating and floating motion of the disc is very important to keep the disc self-cleaning and also prevent blood clotting. However, there is one point during the operation of the valve when it is imperative that the disc remain completely at rest and immovable, and this is when the valve is in closed condition. When the valve is closed, the disc should be motionless and not wobble or vibrate under the pressure of the blood to prevent any leakage through the valve in the no-flow direction. The secure holding of disc 19 when in closed position is therefore very important to prevent it from experiencing any kind of motion, and this holding is accomplished by the wedging of protuberance 21 between post 22' and guide plate 24.

Figure 6:
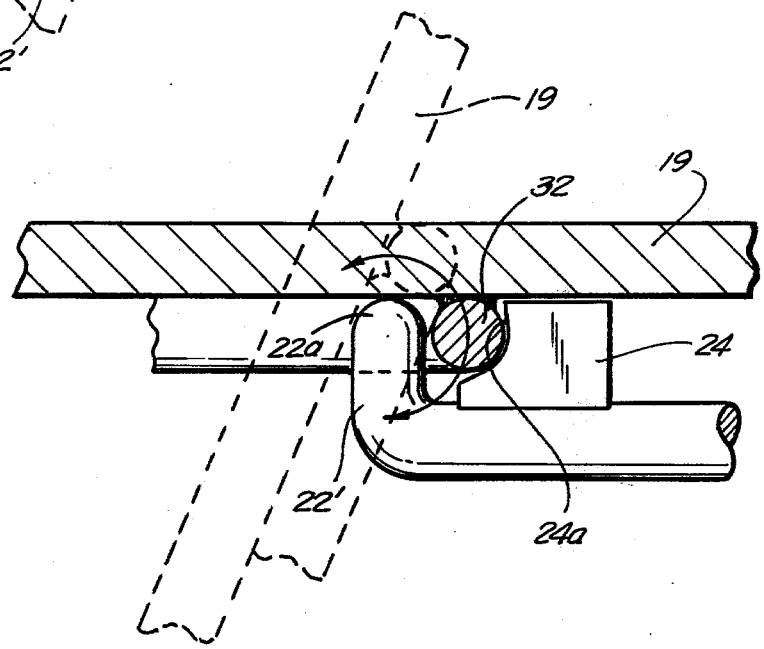
FIG. 6 is a view similar to FIG. 5 showing an alternative embodiment of the ring-like protuberance on the downstream side of the disc.
Figure 7:
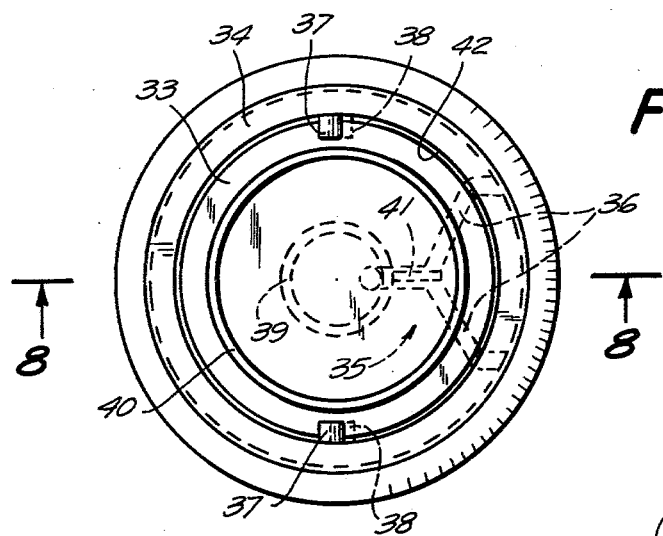
FIG. 7 is a plan view of a second embodiment of the present invention, the valve being shown in closed condition.

In the embodiment of FIGS. 1–5, protuberance 21 is formed by machining so that it is one piece with disc 19. Another form of the ring-like protuberance is illustrated in FIG. 6. This embodiment is identical to the description given above of the interaction of the protuberance 21 with fulcrum member 22 and guide plate 24, but the protuberance is in this case made of a length of circular cross-section wire 32 bent into a continuous ring and welded or otherwise joined to disc 19.

A further embodiment of the invention is illustrated in FIGS. 7–10. In some cases, it is necessary or desirable to insert into the patient's heart a valve which is of extremely light weight and low profile. When the valve shown in FIGS. 1–4 is closed, disc 19 is at an acute angle to the plane of the valve body. The advantage of this design is that the opening of the valve with the disc starting in closed position at an acute angle reduces the distance the disc must travel to reach its open position. But the consequence of starting the pivoting of the disc from an angled position is the necessity to keep the height, i.e., axial dimension, of the valve body relatively large, which also increases the weight of the valve.

Figure 8:
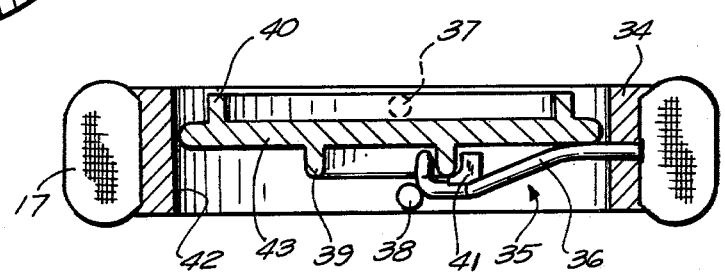
FIG. 8 is a vertical cross-sectional view taken along line 8—8 of FIG. 7.
Figure 9:
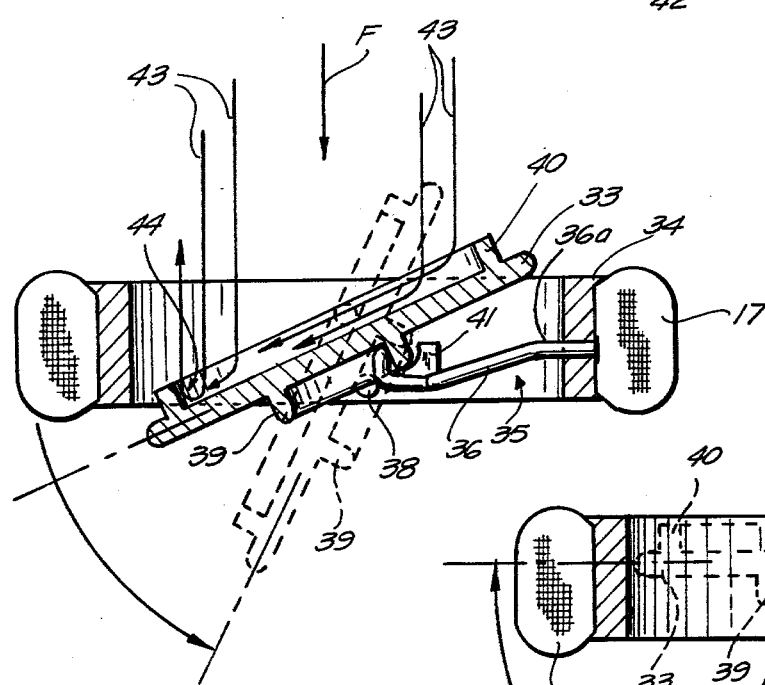
FIG. 9 is a view similar to FIG. 8, the valve being shown moving to its open condition.
Figure 10:
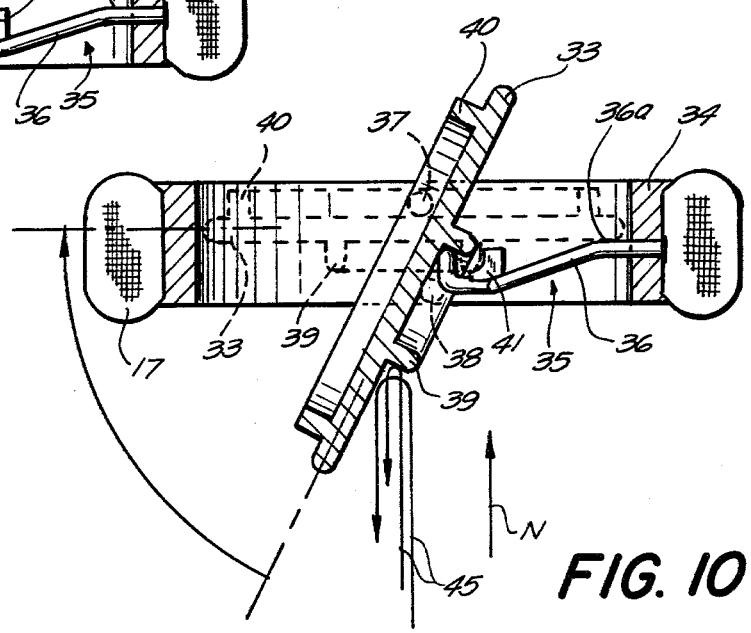
FIG. 10 is a view similar to FIG. 9, the valve being shown in open condition in solid lines.

To produce a valve of very low height and little weight, the valve shown in FIGS. 7–10 is employed, since disc 33 is in a horizontal position, i.e., in the plane of valve body 34, when the valve is closed. Disc 33 is equipped on its upstream side, with an upstanding wall 40, and a fulcrum member 35 carries a guide plate 41. Also, struts 36 are shaped to provide a seat 36a for disc 33 when the valve is in closed condition, as shown in FIG. 8, thereby saving the need for an additional abutment used to define the closed position of the valve disc. On its downstream side, disc 33 is equipped with the ring-like protuberance 39. Valve body 34 is provided with a pair of pins 37 projecting into the central opening 42 from the inner surface of the valve body. The disc 33 fits loosely between retaining pins 37 and the free end of fulcrum member 35, and therefore is able to pivot between open and closed positions and to rotate in its own plane at the same time. Another pair of pins 38 projecting into opening 42 serve as abutments defining the open position of disc 33, as indicated in FIG. 10. Disc 33 pivots around the upstanding free end of fulcrum member 35, which engages the inner surface of protuberance 39 at a point slightly eccentric to the center of the disc, thereby causing disc 33 to pivot in response to pressure differences of the blood stream on opposite sides of the disc.

FIG. 9 shows the valve in operation. As soon as the bloodstream, indicated by the arrows 43 and flowing in the direction of arrow F, arrives at the surface of the disc it starts tilting the disc. The blood then flows along the tilted surface into pocket 44, created by the wall 40 and the surface of the disc 33, which produces a turbine effect compelling disc 33 to quickly swing to its open position, shown in broken lines in FIG. 9. Upon reverse flow of the blood, indicated by arrows 45 in FIG. 10, in the no-flow direction (arrow N) of the valve, the blood flows against a pocket formed by the outer surface of protuberance 39 and disc 33. As a result of this pocket, a turbine effect is created to swing disc 33 speedily from the open solid line position of FIG. 10 to the closed broken line position.

The embodiment of FIGS. 7–10 permits considerable reduction of the weight of the valve and the height of its profile by reducing the size of the valve body. In other respects this valve is similar to the valve shown in FIGS. 1–4.

Another embodiment of this invention is shown in FIGS. 11 and 12. This valve is identical to the one illustrated in FIGS. 7–10, with two exceptions. First, the pivoting disc 46 is completely flat on its upstream side, i.e., there is no wall corresponding to wall 40. Second, guide plate 41 is not present. This arrangement represents an additional economizing of the design and makes the valve still lighter in weight. In all other respects the valve is similar to the one shown in FIGS. 7–10. However, this valve does not open as quickly as the valve of FIGS. 7–10 because of the absence of the turbine effect produced by wall 40, and disc 46 is subject to vibration and wobble when in its closed position due to the absence of guide plate 41.

Another embodiment of the invention is shown in FIGS. 13 and 14. This valve is identical to the valve of FIGS. 11 and 12, except that fulcrum member 48 is of a different form, and carries a guide plate 50. Fulcrum member 48 comprises two struts 49 arranged in the form of a letter "V", a post 51, which cooperates with protuberance 39, projecting upwardly from the apex of the "V". A platform 52 extends between struts 49 and supports plate 50. This valve operates in the same manner as the valve of FIGS. 11 and 12, except that it has the advantage of the presence of guide plate 50.

FIG. 15 shows another alternative fulcrum member 55 formed in part of a single piece of wire. The wire is provided with three bends, one bend 56 being at its centerpoint, and two bends 57 being spaced on either side of bend 56. The bends define two struts 58 merging into a double-legged upstanding post 59. The free end 56 of post 59 cooperates with the circular protuberance projecting from the valve disc with which the fulcrum member is used, and struts 58 are fixed to the body of the valve, as described above with respect to the other fulcrum members. A platform 60 extends between struts 58 and supports a guide plate 61, for the purpose described above with respect to guide plates 24, 41, and 50.

FIG. 16 shows a fulcrum member 55' identical to fulcrum member 55 of FIG. 15, except that platform 60 and guide plate 61 are absent. This fulcrum member can serve in place of the fulcrum member shown in FIGS. 11 and 12.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

What is claimed is:

1. A prosthetic one-way heart valve comprising:
   (a) a generally annular valve body having a central opening defining a blood flow passageway,
   (b) a disc within said valve body and having a periphery substantially complementary to the periphery of said opening, and
   (c) means supporting said disc for pivotal movement, with respect to said body, between a position in which blood is permitted to flow through said body and a position in which flow of blood through said body is blocked, said means including:
      (I) a ring-like protuberance projecting from one face of said disc in the general direction of flow through the valve, said protuberance being radially spaced from the peripheral edge of said disc to define an abutment responsive to fluid flowing in the no-flow direction of the valve for aiding pivotal movement of said disc to a position in which the valve is closed, and
      (II) fulcrum means projecting into the central opening from said valve body, said fulcrum means engaging the inner surface of said protuberance such that said disc pivots about said fulcrum means.

2. A prosthetic one-way heart valve as defined in claim 1 including an upstanding wall projecting from the face of said disc opposite the face carrying said ring-like protuberance, said wall being continuous and unbroken throughout its length.

3. A prosthetic one-way heart valve as defined in claim 2 wherein said wall is circular and located closer to the periphery of said disc than said ring-like protuberance.

4. A prosthetic one-way heart valve as defined in claim 2 wherein the total combined height of said wall, said protuberance, and the thickness of said disc is no greater than the axial dimension of said valve body, so that when the valve is closed the disc, wall and protuberance are contained entirely within the contour of said valve body.

5. A prosthetic one-way heart valve as defined in claim 1 wherein said fulcrum means carries an upstanding post at its free end extending generally in the axial direction of said valve body, the free end of said post engaging the inner surface of said protuberance.

6. A prosthetic one-way heart valve as defined in claim 5 including guide means carried by said fulcrum means, said guide means being spaced from said post, and said protuberance being captured between said post and guide means when the valve is closed to prevent movement of said disc in its own plane.

7. A prosthetic one-way heart valve as defined in claim 6 wherein said guide means includes a thin plate projecting from said fulcrum means in the axial direction of said valve body.

8. A prosthetic one-way heart valve as defined in claim 1 including a seat against which said disc abuts when the valve is closed, a part of said fulcrum means defining said seat.

9. A prosthetic one-way heart valve as defined in claim 5 wherein said fulcrum means includes a pair of struts projecting from said valve body in the general shape of a letter "V", said post projecting from the apex of the "V".

10. A prosthetic one-way heart valve as defined in claim 9 including a platform extending between said struts, and guide means carried by said platform, said guide means being spaced from said post, and said protuberance being captured between said post and guide means when the valve closed to prevent movement of said disc in its own plane.

11. A prosthetic one-way heart valve as defined in claim 1 wherein said ring-like protuberance is an annulus of wire having a circular cross-section, said annulus being permanently fixed to said disc.

12. A prosthetic one-way heart valve as defined in claim 1 wherein said fulcrum means comprises a length of wire bent to define two converging struts which merge into a double-legged upstanding post, the free end of said post engaging the inner surface of said protuberance.

* * * * *